United States Patent [19]

Cohen et al.

[11] Patent Number: 4,686,963

[45] Date of Patent: Aug. 18, 1987

[54] TORSION RESISTANT VERTEBRATED PROBE OF SIMPLE CONSTRUCTION

[75] Inventors: Jack Cohen, Norwalk; John L. Wardle, Wilton, both of Conn.

[73] Assignee: Circon Corporation, Santa Barbara, Calif.

[21] Appl. No.: 836,434

[22] Filed: Mar. 5, 1986

[51] Int. Cl.$^4$ ................................................ A61B 1/00
[52] U.S. Cl. ........................................ 128/4; 138/120; 350/96.26
[58] Field of Search ................ 128/4, 6, 11; 138/120; 350/96.26

[56] References Cited

U.S. PATENT DOCUMENTS

| | | | |
|---|---|---|---|
| 2,975,785 | 3/1961 | Sheldon | 128/6 |
| 3,190,286 | 6/1965 | Stokes | 128/6 |
| 3,266,059 | 8/1966 | Stelle | 128/4 X |
| 3,557,780 | 1/1971 | Sato | 128/4 |
| 3,799,151 | 3/1974 | Fukaumi et al. | 128/6 |
| 3,913,568 | 10/1975 | Carpenter | 128/11 |
| 4,530,568 | 7/1985 | Haduch et al. | 128/6 X |

FOREIGN PATENT DOCUMENTS 179905 10/1954 Austria .

*Primary Examiner*—William H. Grieb
*Attorney, Agent, or Firm*—Perman & Green

[57] ABSTRACT

An inspection instrument has an elongated flexible body which extends between a control assembly at a proximal end and an objective head at a distal end. Fiber optic bundles disposed within the instrument permit the illumination and the imaging of the interior regions of a structure being inspected. An articulating vertebrae assembly and a transitional coupler are disposed proximally of the objective head whereby the objective head is caused to move in an arc when tension is applied to interiorly disposed cables connecting the objective head to the control assembly. The vertebrae assembly is comprised of individual hollow vertebrae which are disposed along and axially aligned by a resilient stiffening member which is fixed at a distal end within the objective head and at a proximal end within the coupler. The member provides flexibility to the vertebrae assembly and, because it has a rectangular cross-sectional area, resists a torsion about its longitudinal axis, thus making the distal end of the instrument torque stable.

27 Claims, 19 Drawing Figures

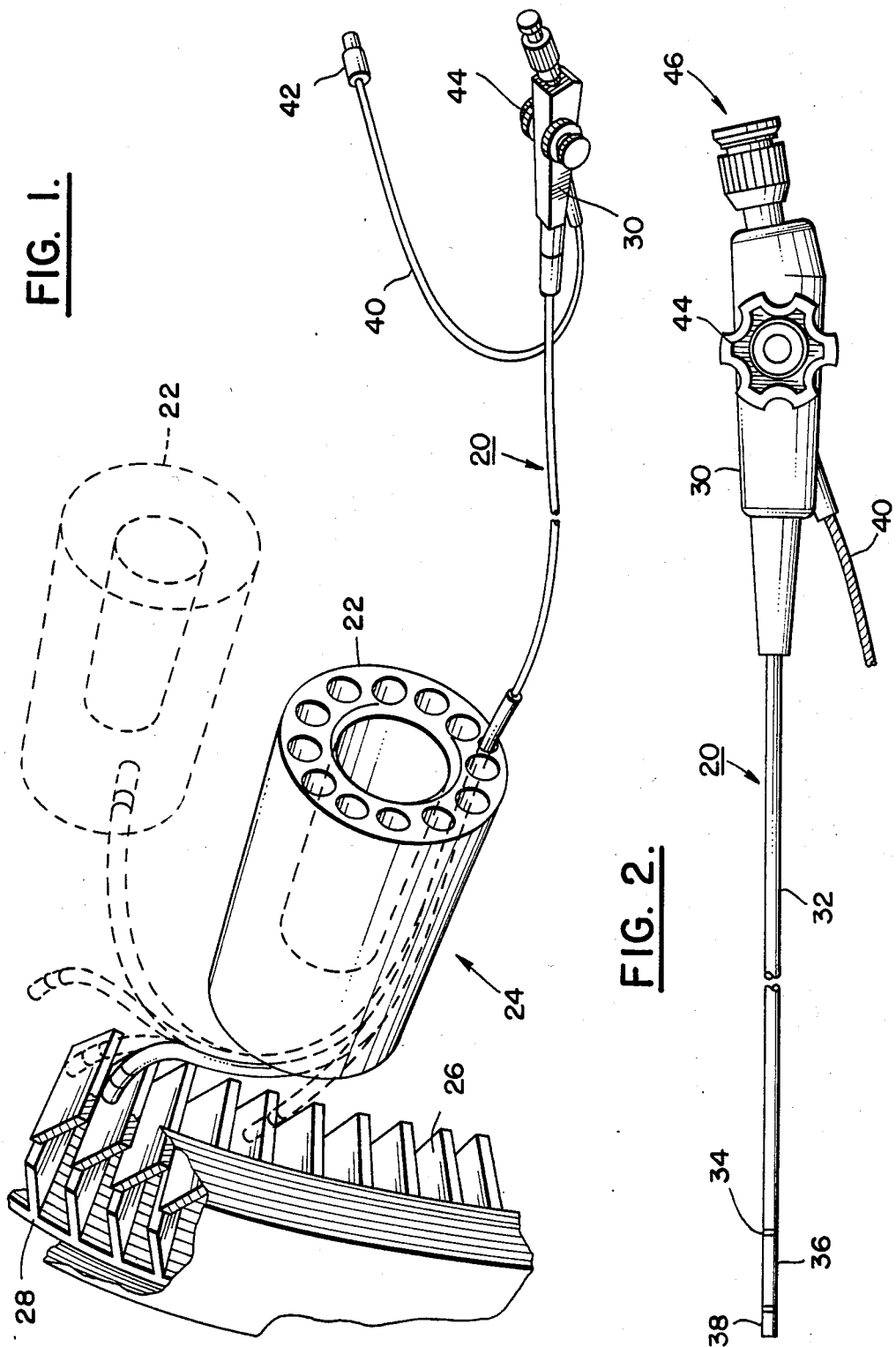

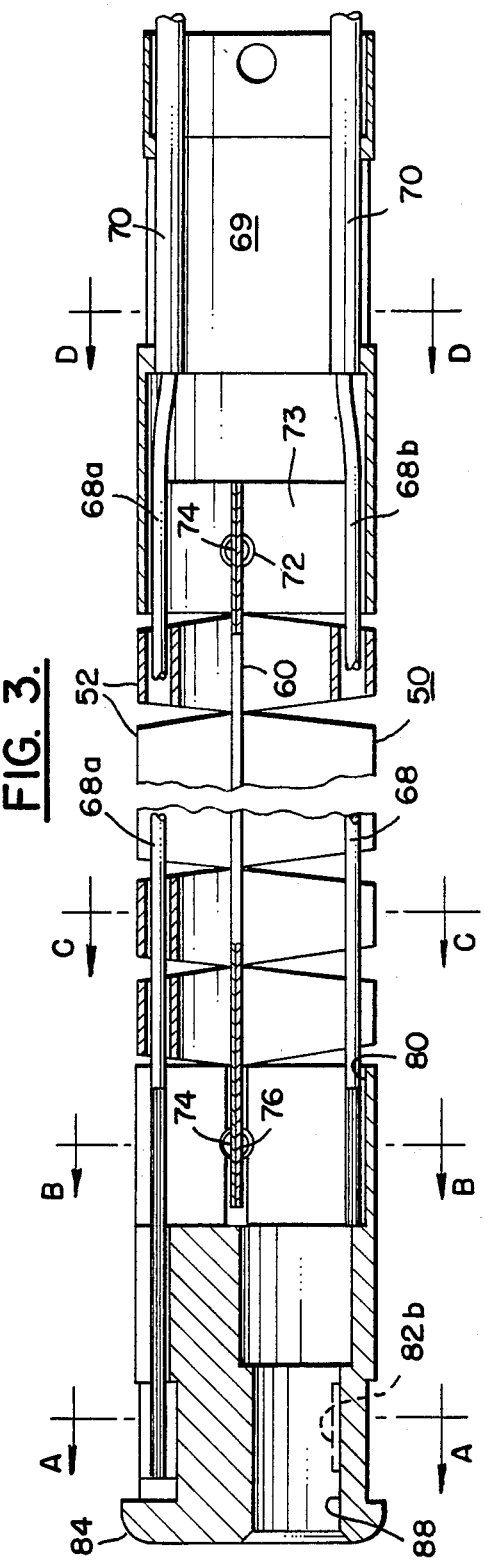
FIG. 3.
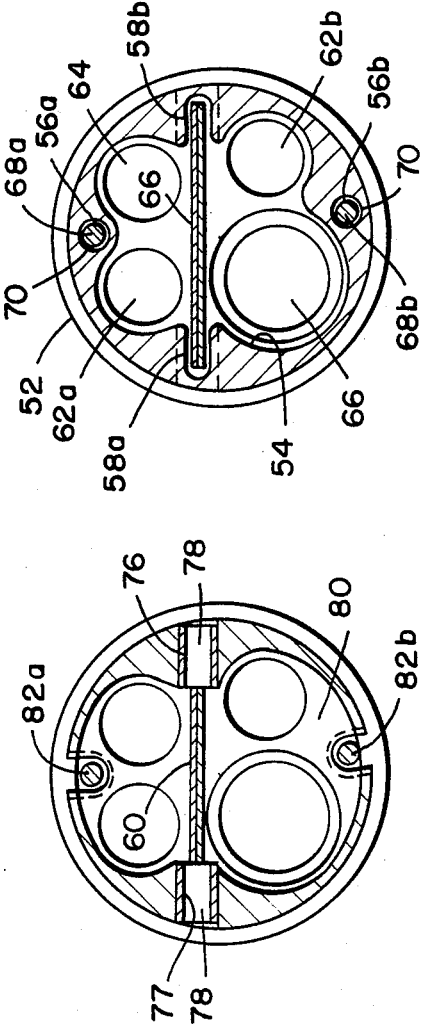
FIG. 3C.
FIG. 3B.
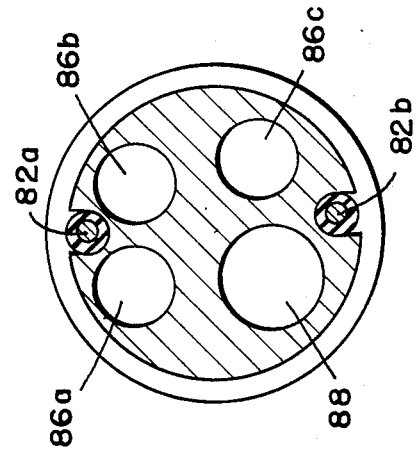
FIG. 3A.

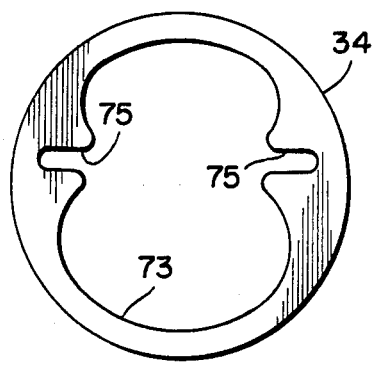
FIG. 6.
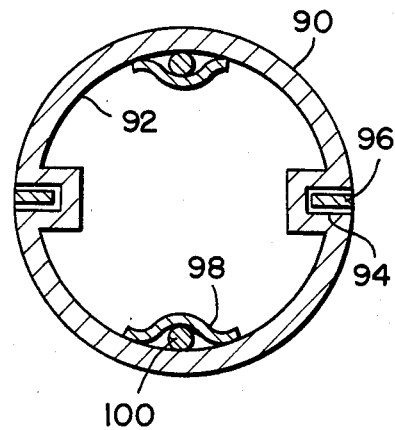
FIG. 8.
FIG. 7.
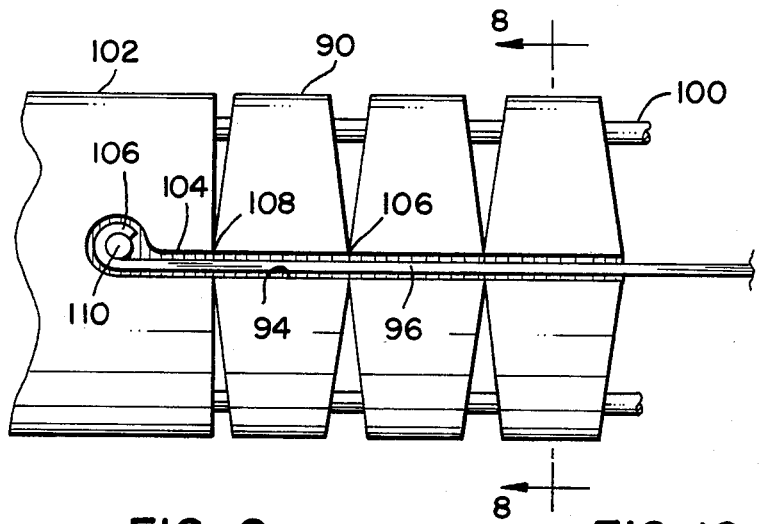
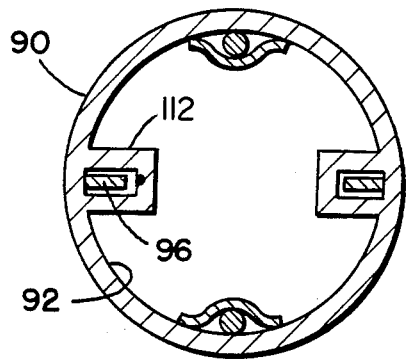
FIG. 9.
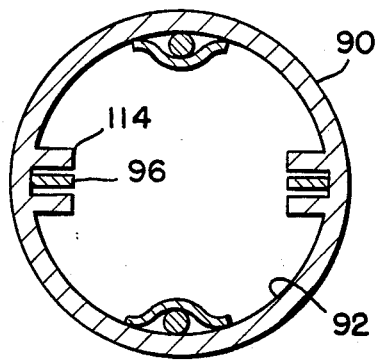
FIG. 10.

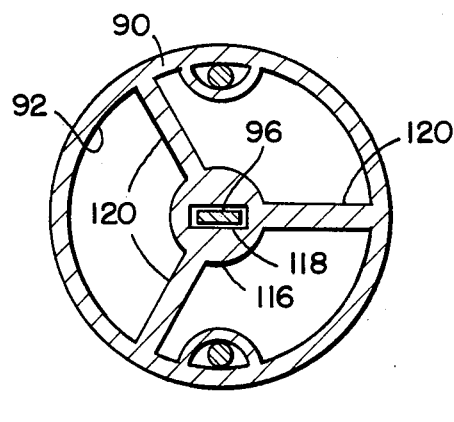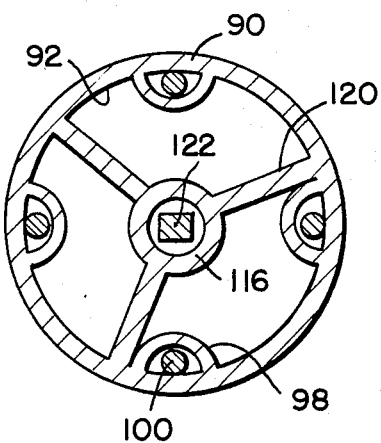

TORSION RESISTANT VERTEBRATED PROBE OF SIMPLE CONSTRUCTION

BACKGROUND OF THE INVENTION

This invention relates to a flexible inspection system for use in both industrial and medical applications and, more particularly, to an elongated, flexible, fiber-scopic inspection device having an articulating vertebrae assembly disposed along a flexible stiffening member.

It can be readily appreciated that the capability to inspect the internal cavities within a complex mechanical structure, without requiring the disassembly of the structure, is a valuable feature of an inspection system. One such mechanical structure is a jet engine. The use of a flexible inspection device allows for the internal inspection, on a routine basis, of those areas of the engine that are most susceptable to wear and fatigue. The rotor and stator blades within the high temperature first stage of the engine is one such area. Regularly scheduled, routine inspection of the first stages of the engines of a jet aircraft can detect a deteriorating component before such a component fails with a potentially catastrophic loss of human life. If it were required to disassemble the engines each time they were to be inspected, such inspections would, for obvious economic reasons, not occur as frequently.

Another highly valuable application for a flexible inspection device is in the diagnostic evaluation of various cavities within the human body. The colon is such a cavity where a form of the device, known generally as an endoscope, is utilized by physicians to examine the inner walls for abnormalities. Typically, the physician peers through an eyepiece located on a control mechanism while manipulating control knobs, thereby guiding the probe tip while advancing it through the colon and simultaneously examining the inner wall thereof. The eye piece is located at the proximal end of a fiber-optic bundle, the bundle typically being enclosed within a flexible tube. The distal end of the flexible tube terminates in an objective head. Cables connected to the control knobs extend through the flexible tube to the objective head. The manipulation of the control knobs varies the tension within the cables, thus effectuating a lateral movement of the distal probe end whereby the distal end can be guided through the convolutions of the lower bowel. Also enclosing within the flexible tube are, typically, one or more additional fiber optic bundles for the purpose of illuminating the area being viewed, the source of the illumination being a lamp coupled to the proximal end of these bundles. If desired, the endoscope can further incorporate a channel for conveying a washing solution to the distal end, as well as a surgical tip and other useful features.

The industrial corollary of the endoscope is typically known as a borescope, an application for which was described above as an inspection instrument for jet engines. The construction principles of both instruments, namely the endoscope and the borescope, are similar. The differences between the instruments typically being in the dimensions of the flexible tube and the nature of the protective sheath covering the tube. For instance, the flexible tube of a borescope may be required to be enclosed within a jacket of metal braid or some similar rugged material, while such a sheath would be inappropriate for use with an endoscope.

As may well be appreciated, an important component of a flexible inspection instrument is the region adjacent to the distal end where the articulation of the objective head is effectuated. Such a region is typically comprised of the objective head, wherein the optical elements and the control cables terminate, an adjacent chain of articulating vertebrae, which provide for precisely manipulating the objective head, and a coupler whereby the chain of articulating vertebrae are coupled to the flexible tube. In the past various methods of interconnecting the individual articulating vertebrae have been devised, the goal of each method to provide an articulating member capable of precisely controlled movement, flexibility, and structural strength and integrity.

One typical method to accomplish these goals is to join adjacent vertebrae together with pins, the vertebrae being shaped such that they may pivot relative to one another about the pins. Illustrative of such a prior art joining technique are U.S. Pat. Nos. 3,799,151, and 4,530,568, said last U.S. Patent assigned to the assignee of the present invention. The method of joining the vertebrae shown and described in the above mentioned prior art, while suitable for forming a chain of articulating vertebrae, is also disadvantageous for several reasons.

One problem arising from such a pinning method is that a complicated and costly assembly procedure is required to pin each vertebrae to the two adjacent vertebrae, due to the small size of both the vertebrae and the pins, and to the number of vertebrae required to be joined, a typical value being 18 or more.

Another problem with this type of prior art joining technique is that a lower design limit is reached on the size of the individual elements. As the physical dimensions of the vertebrae and pins are scaled down for small caliper assemblies, the assembly procedure becomes even more difficult and costly.

Another disadvantage of the prior art method of joining the individual vertebrae by pinning results from each pivot point having a characteristic amount of friction associated with it. The friction characteristics of each pivot point are typically different from one another, the difference being due to the normal physical tolerances of the individual elements. Thus, a differing degree of articulation may be present in various regions along the chain of vertebrae, resulting in a non-uniform curvature of the articulating vertebrae assembly.

Another less obvious problem with this prior art joining technique is that as the number of individual components, represented by vertebrae and pins, of the chain of articulating vertebrae increases, the overall reliability decreases as there is an increased probability of individual component failure.

To overcome these problems it has been known in the prior art to join the individual vertebrae together with two or more wires of small cross-sectional diameter which are threaded through holes made longitudinally through the vertebrae. Illustrative of this prior art joining method are U.S. Pat. Nos. 3,190,286 and 3,557,780. U.S. Pat. No. 3,557,780, to M. Sato, which patent is incorporated herein by reference, describes a mechanism for controlling the flexure of an endoscope wherein articulated segments have opposing faces tapered to form diametrically extending pivot ridges. The pivot ridges are flexibly urged together by two wires, one of each of the wires passing through two diametrically opposed small holes which are provided through the segments at positions in the pivot ridges. U.S. Pat. No. 3,190,286, to R. Stokes, which patent is also incorporated herein by reference, discloses a flexible viewing probe comprised of segments having holes disposed 90 degrees apart, pivot elements interposed between the segments, and a control wire or cord passing through each hole and pivot element whereby the probe may be controllably flexed by the movement of the segments about the pivot elements.

The aforementioned prior art method of joining the vertebrae by the use of two or more wires, although embodying a simpler mechanical principle than the aforementioned method of pinning adjacent vertebrae together, suffers from the problem that the probe may experience an undesirable torsion or twist about its longitudinal axis. Such a torsion may occur when the probe body or objective head is subjected to a tangential force, such as may be encountered in the complex movements the device makes within the cavity being inspected. The tensioning forces imparted by the control cables may also cause the probe body to undergo a torque, if such tensioning forces are unbalanced either by design or inadvertently during operation. This susceptibility to torqueing forces, resulting in an undesirable torsion about the longitudinal axis of the probe tip, is due to the tendency of the internally disposed joining or control wires to twist about their longitudinal axis when subjected to a torque.

It has also been known in the prior art to join the individual vertebrae together by the use of a pair of flexure strips which are secured to spaced apart vertebrae by welding, cementing, or tongue and groove means. Illustrative of such a method is U.S. Pat. No. 2,975,785 to G. Sheldon, which patent is herein incorporated by reference.

One disadvantage of this method is that because the flexure strips are rigidly secured along each of the vertebrae, that the flexure must occur in that portion of the flexure strips between adjacent vertebrae. Thus the stresses due to bending which are induced within the flexure strips are localized to those regions between vertebrae, rendering the flexure strips more susceptable to stress induced cracking and failure.

Another problem with this prior art method is that the overall degree of curvature of a given length of such a vertebrae assembly is limited to that which can be accomplished within that portion of the flexure strips not rigidly attached to the vertebrae. All of the flexure must, therefore, occur in that region of the flexure strips between adjacent, spaced apart vertebrae. As may be realized, if a greater degree of curvature is desired, the overall length of the vertebrae assembly so joined together must be made correspondingly longer, which in some applications may not be practical.

SUMMARY OF THE INVENTION

The foregoing problems are overcome and other advantages are provided by a vertebrae assembly having a torsion inhibiting resilient stiffening means. The vertebrae assembly has a base end member and an articulating end member, with a plurality of individual articulating vertebrae disposed therebetween, the vertebrae being disposed along the stiffening means in a manner such that the vertebrae are moveably coupled with the stiffening means. The assembly is held together by a fastening means which is attached to the base end member and the articulating end member.

In one embodiment of the invention the vertebrae assembly forms part of a flexible inspection device having a control assembly, an objective, or distal, head, and an elongated flexible body therebetween. The vertebrae assembly is disposed such that its base end member joins to the flexible body, and its articulating end forms the objective head of the inspection device. The resilient stiffening means is attached to the base end member and the objective head such that it serves both to fasten the assembly together and also give it flexibility.

In a further embodiment of the invention the stiffening means is disposed in the center region of each of a plurality of annular vertebrae, the stiffening means being supported within channels within the vertebrae. In a still further embodiment of the invention, two separately acting stiffening members are disposed along annular vertebrae, each stiffening means being supported in a different region of the vertebrae. In yet another embodiment of the invention the stiffening means is centrally disposed within a plurality of annular vertebrae, each vertebrae having spoke-like supports which locate and support the stiffening means.

BRIEF DESCRIPTION OF THE DRAWINGS

The foregoing aspects and other features of the invention are explained in the following description, taken in connection with the accompanying drawings wherein:

FIG. 1 is a stylized view of an inspection instrument incorporating the invention for viewing the interior region of a jet engine;

FIG. 2 is a plan view of the instrument of FIG. 1;

FIG. 3 is a partially cut away sectional view of the distal articulating section of the instrument of FIG. 1;

FIGS. 3A, 3B, 3C, and 3D are transverse sectional views taken along the the lines A—A, B—B, C—C and D—D, respectively, in the drawing of FIG. 3;

FIG. 6 is a profile view of a forward aperture within the transitional coupler of FIG. 3;

FIG. 7 is a partial side view of the distal articulating section of the instrument of FIG. 1 having an alternate embodiment of the invention.

FIG. 8 is a cross sectional view of a vertebrae taken along the line 8—8 of FIG. 7; and FIGS. 9, 10, 11 and 12 are each a cross-sectional view of a vertebrae having alternate embodiments of the invention.

DETAILED DESCRIPTION OF THE INVENTION

Figure 3D:
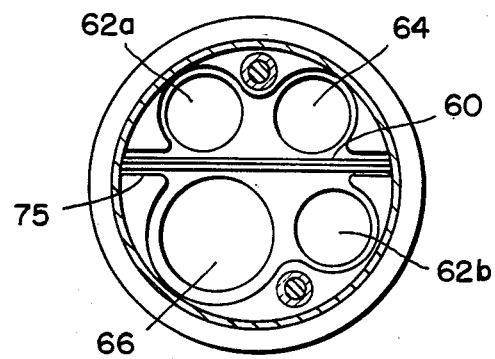

This invention can be utilized in any suitable device in which a controlled, torsion resistant articulation is required. For the purposes of this description, however, the invention is disclosed in the environment of a flexible inspection device for industrial applications. Such an inspection device can be used equally as well for medical applications.

An inspection instrument 20, as shown in FIGS. 1 and 2, is constructed with an elongated tubular form and incorporates the invention so as to permit passage of the objective head 38 through a complex mechanical structure such as a jet engine 24. Typically the instrument would be inserted through an opening in a burner can 22, passing therethrough so as to inspect the blades of the rotor 28 and the stator 26 and the interior regions of the burner can 22 itself.

Inspection instrument 20 is substantially comprised of a control assembly 30, a flexible tube, or shaft, 32, a transitional coupler 34, an articulating vertebrae assembly 36, and an objective, or distal, head 38. A light conduit 40 conveys illumination in a conventional manner from a lamp box (not shown) through the control assembly 30 to the objective head 38 by way of a bundle or bundles of light transmissive fibers (not shown in FIGS. 1 and 2). The light so transmitted exits the objective head to illuminate the area to be examined. Conduit 40 connects to the lamp box (not shown) by means of a connector 42. Disposed on control assembly 30 are control knobs 44. Rotation of control knobs 44 varies the tension within one or more control cables (not shown in FIGS. 1 and 2). One method for varying the tension within such control cables is described in U.S Pat. No. 4,530,568, to R. Haduch et al., this patent assigned to the assignee of the present invention. This patent is herein incorporated by reference. The control cables are fixed at a distal end to objective head 38, thereby causing varying degrees of flexure to occur in the articulating vertebrae assembly 36 disposed behind objective head 38. Objective head 38 is rigidly coupled to a forward end of vertebrae assembly 36 such that objective head 38 is caused to flex up and down in a vertical arc. An eyepiece 46 is disposed upon control assembly 30 and provides for the imaging of the area under inspection. Imaging light enters objective head 38 and is transmitted by way of a bundle of light transmissive fibers (not shown in FIGS. 1 and 2) through the instrument 20 to eyepiece 46.

As shown in greater detail in FIG. 3, the forward section of instument 20, in accordance with an embodiment of the invention, is substantially comprised of a base end member, herein called a transitional coupler 34, an articulating vertebrae assembly 36, and an articulating end member, herein called an objective, or distal, head 38.

Figure 5A:
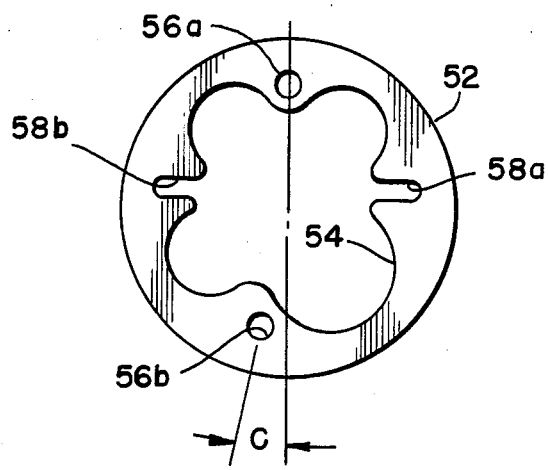
FIG. 5A is an end view of an articulating vertebrae taken in the direction A of FIG. 5.
Figure 5:
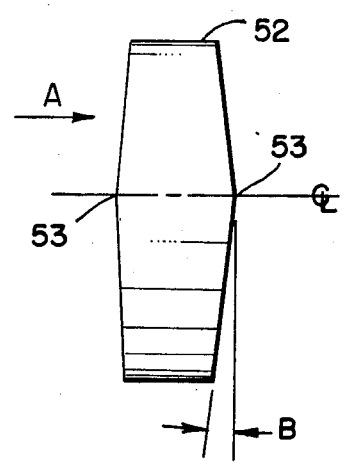
FIG. 5 is a side view of an articulating vertebrae showing the outwardly extending tapered ridges.

Vertebrae assembly 36 is comprised of a plurality of vertebrae 52, each of which has the characteristics as shown in FIG. 5. It can be seen that a vertebrae 52 is of a substantially annular shape having opposing faces tapered to form off-centered diametrically extending pivot ridges 53. The angle of taper, shown in FIG. 5 as B, is generally known as the operating angle, and defines the greatest amount of pivotal movement allowed a vertebrae about the pivot ridge 53. A representative value for B may be 10 degrees, but any suitable value may be utilized depending upon the amount of overall curvature required by a particular application.

Although the vertebrae 52 shown is of a substantially annular shape, any suitable shape, such as an oval or polygonal shape, can be utilized so long as the vertebrae are able to articulate one to another in a controlled fashion and also contain apertures for various through channels.

FIG. 5A is an end view of the vertebrae of FIG. 5 taken in the direction indicated by the arrow A that shows a major aperture 54 having two diametrically opposed indentations formed in its wall. These indentations are a first supporting channel 58a and second supporting channel 58b. Channels 58a and 58b are symetrically disposed about a plane that passes through the pivot ridges 53. The width and planar disposition of channels 58a and 58b will be more fully discussed hereinafter.

Vertebrae 52 also has an on-axis minor aperture 56a disposed symetrically about a vertical centerline and an off-axis minor aperture 56b disposed at an angle C from the centerline. Referring to FIG. 3 it can be seen that an on-axis control cable 68a passes through aperture 56a and that an off-axis control cable 68b passes through aperture 56b. The degree to which one or both of the central cables may be offset from the vertical centerline is a function of the size and number of elements which must pass through the vertebrae, depending on the particular intended application. Preferrably, vertebrae 52 is composed of a high strength material such as, typically, stainless steel, and is of dimensions that are appropriate for the intended application of the inspection instrument 20. However, it should be realized that any suitable material may be used in the construction of the vertebrae 52.

In order that a vertebrae 52 may pivot relative to pivot ridges 53 and, hence, function as a component of the articulating vertebrae assembly 36 it is necessary to axially align a plurality of vertebrae 52 along their pivot ridges 53 and maintain adjacent pivot ridges in contact with one another under varying degrees of flexure. As was previously discussed, it is known in the prior art to utilize pins or internally disposed wires or securely attached flexure strips to accomplish and maintain this alignment, these methods however having the aforementioned disadvantages of structural complexity, low resistance to torqueing forces, or a low resistance to bending stress induced cracking.

Figures 4A, 4B:
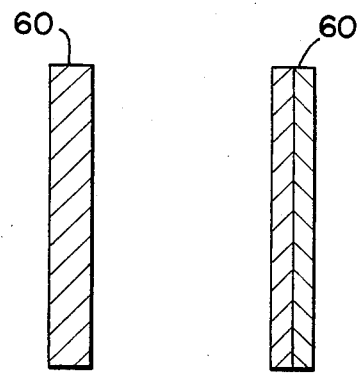
FIG. 4A is a transverse sectional view taken along the line A—A of the drawing of FIG. 4 showing one embodiment of the invention.
FIG. 4B is a transverse sectional view taken along the line A—A of the drawing of FIG. 4 showing an alternate embodiment of the invention.
Figure 4:
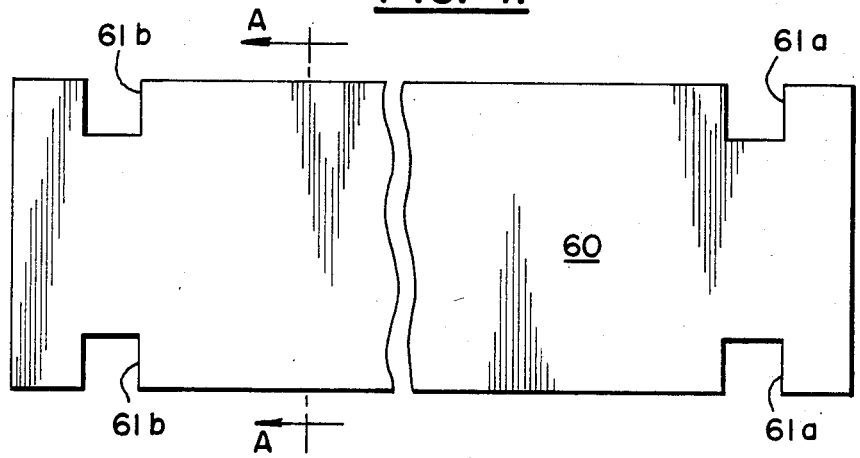
FIG. 4 is a top view of a resilient stiffening member which is an important feature of the invention.

In this embodiment of the invention these disadvantages are overcome by the use of a resilient stiffening member 60, as seen in FIG. 4 and 4A and 4B, FIGS. 4A and $b each being a transverse sectional view taken along the line A—A of FIG. 4 showing alternate embodiments of the instant invention. The member 60 is of a substantially rectangular shape and a substantially rectangular cross section. Referring to FIGS. 3 and 3C it can be seen that member 60 is disposed such that it engages and is moveably coupled within the supporting channels 58a and 58b of each vertebrae 52 along its outer longitudinal edges. As was previously discussed, channels 58a and 58b are symetrically disposed along the horizontal plane which passes through opposing pivot ridges 53, thus member 60 will also be disposed along this plane. Member 60 has sufficient stiffness to maintain adjacent pivot ridges 53 of adjacent vertebrae 52 in axial alignment, and sufficient flexibility to permit vertebrae 52 to rotatably pivot about pivot ridges 53. Supporting channels 58a and 58b must provide for sufficient clearance to allow the resilient member 60 to flex within channels 58a and 58b, such that excessive bending stresses are not induced in member 60 at the pivot ridges 53. Unlike devices in the prior art where flexure strips are secured to each of the spaced-apart vertebrae, such that all flexure must occur between the vertebrae, it can be seen that member 60 is moveably coupled to each of the vertebrae 52, thus allowing for a substantially uniform flexure along the length of member 60. Thus, flexure stresses that may be induced are distributed and are not localized, as in the prior art, resulting in a vertebrae assembly 36 that is better suited for flexing.

In order to further minimize the flexure stresses within the resilient member 60, it may be advantageous in some applications that member 60 be comprised of two or more members, each member of a thickness such that when two or more members are stackably arranged in a leaf-like spring assembly, that the overall thickness will be appropriate for the degree of flexure being imposed on it. A member 60 comprised of such a leaf-like spring assembly is more resistant to cracking and mechanical failure, induced by flexing, in that each constituent member, being made thinner, is more flexible and hence more suitable for being flexed. FIG. 4B shows an alternate embodiment of FIG. 4A wherein it can be seen that member 60 is comprised of two members having a total thickness equal to the thickness of the embodiment of FIG. 4A. Likewise, member 60 could be comprised of three or more members, so long as the total overall thickness is suitable for being contained within supporting channels 58.

In order that adjacent pivot ridges 53 of adjacent vertebrae 52 provide operable pivot points it is necessary that adjacent ridges 53 be butted one against the other and remain in contact with one another when vertebrae assembly 36 is in a flexed position.

This is accomplished in the invention by securing member 60 at a rear portion to transitional coupler 34 and at a forward portion to objective head 38 by the use of pins 74 which are inserted through a pair of coupler pinning apertures 72 and objective pinning apertures 76.

Referring to FIG. 4 it can be seen that two opposing rear slots 61a are formed in a rear portion of member 60 for engaging pins 74. Likewise, two opposing forward slots 61b are formed in a forward portion of member 60 for engaging pins 74. The length of member 60, the placement of slots 61a and 61b relative to the ends of member 60, and the location of pinning apertures 72 and 76 are selected such that when member 60 is pinned that the plurality of vertebrae 52 interposed between coupler 34 and objective head 38 are urged towards one another. Adjacent vertebrae 52 are maintained in contact during flexing of vertebrae assembly 36, preferrably thereby maintaining adjacent pivot ridges 53 in pivotal contact. The pivot ridges 53 at the extreme ends of vertebrae assembly 36 are likewise urged against opposing vertically planar surfaces at the forward end of coupler 34 and at the rearward end of objective head 38, pivot ridges 53 thereby pivoting against these surfaces.

Although member 60 has been shown to be pinned at each end, it should be realized that any suitable fastening means may be utilized so long as member 60 is securely fastened such that the pivot ridges 53 are maintained in pivotal contact.

As seen in FIGS. 3 and 3D, transitional coupler 34 is of approximately cylindrical shape having a centrally disposed opening therethrough. A rearward end of coupler 34 has a circular aperture 69 made therein whereby a first and second transmission bundle, 62a and 62b respectively, an image bundle 64, the aforesaid on-axis and off-axis control cables, 68a and 68b respectively, and a working channel 66 enter from flexible tube 32. Transmission bundles 62a and 62b convey the aforementioned illumination from the light source to the region to be examined. Similarly image bundle 64 conveys light reflected from such a region back to the eyepiece 46 for viewing by the operator. Bundles 62 and 64 are typically comprised of a plurality of flexible fiber-optic strands having light transmissive qualities along a longitudinal axis, as is well known in the art.

Although the transitional coupler 34 as shown has a particular shape, any suitable shape may be utilized so long as the coupler may act as the base end member for vertebrae assembly 36 and as collar-like coupler means for joining to flexible tube 32.

Control cables 68a and 68b are each typically slidably contained within a protective, flexible sheath 70 as they pass through the length of the flexible tube 32. Cables 68 exit their respective sheaths 70 within coupler 34 so that they may be threaded through the on-axis and off-axis vertebrae minor apertures, 56a and 56b respectively. Control cables 68 are typically comprised of a wire or a strand of wires, such that they possess the characteristics of strength, flexibility, and dimensional stability.

FIG. 6 is a profile view of the forward end of coupler 34 wherein it can be seen that a forward aperture 73 is of a similar shape to that of the vertebrae major aperture 54. Viewing FIG. 6 in conjunction with FIG. 3 it should especially be noted that coupler supporting channels 75 are of equal size and are in registration with the vertebrae supporting channels 58. The aforementioned coupler pinning apertures 72 are disposed through the outer cylindrical wall of coupler 34 such that each one enters an interior region of one of the coupler supporting channels 75, whereby the rear slots 61a of member 60 may be engaged by pins 74, thereby securely fastening the rearward end of member 60 within coupler 34.

Objective head 38 is comprised in part of a rear aperture 80 of substantially the same shape as that of forward coupler aperture 73. Objective pinning apertures 76 are similarly disposed through the outer cylindrical wall of objective head 38 such that the forward end of member 60 may be rigidly fixed by pins 74, thereby aligning and urging vertebrae 52 against one another along their respective pivot ridges 53.

It can be seen at this point that the articulating vertebrae assembly 36 as described above is of a simpler construction and has a lesser number of components than the vertebrae assembly provided by the aforementioned prior art method of pinning each vertebrae to each adjacent vertebrae. Thus assembly 36, in accordance with this embodiment of the invention, has a lower assembly cost and is inherently more reliable. It can also be appreciated that the articulating vertebrae assembly 36, in accordance with this embodiment of the invention, is amenable to a reduction in scale, thus allowing the manufacture of articulating probes of small cross section.

Objective head 38 is further comprised of an on-axis control cable terminator 82a and on off-axis control cable terminator 82b. Terminators 82 are formed as hanger-like structures fixed to the wall of aperture 80 such that they may capture the control cables 68 after they exit the vertebrae assembly 36. Cables 68 are securely anchored to terminators 82 by a suitable method, such as soldering, such that a proximally directed tension force exerted by control assembly 30 upon the control cables 68 will cause a flexure in vertebrae assembly 36, as will be further described hereinafter.

Although control cables 68 are shown to be fastened within hanger-like terminators 82, any suitable fastening means may be utilized so long as control cables 68 are securely anchored within objective head 38.

A plurality of circular channels 86a, 86b, 86c, and 88 within a front face of objective head 38 are disposed such that a front end of each channel 86 and 88 exits the front face of objective head 38 and a rearward end of each opens into the rear aperture 80. Channels 86a, 86b and 86c are of a diameter such that channels 86a and 86c will contain the light transmitting bundles 62a and 62b, and channel 86b will contain the image bundle 64. Optical elements (not shown) such as lenses, may be disposed within channels 86 at or near the front face to facilitate the dispersion or focusing of illuminating light or the collection of imaging light for transmission to the eyepiece 46.

Channel 88 has a diameter that will contain the flexible working conduit 66, whereby a washing fluid may be conveyed through the instrument 20 to the region under inspection. Conduit 66 may also be fitted with a number of different devices, such as a wire snare scapel, thus allowing the operator physical access to the region under inspection.

An outer edge of the front end of objective head 38 is formed as a rounded flange 84 to facilitate the unimpeded movement of head 38 through the interior regions of the structure being inspected.

Although the objective head 38 as described is of a particular shape, it should be realized that any shape may be utilized so long as objective head 38 is suited for use with the intended application of the inspection device and also fulfils the requirements of providing a suitable fastening means for member 60 and control cables 68. It should be realized that in some applications the head 38 need not contain an optical objective element and light illuminating members as described herein, but may contain instead an ultrasonic probe, or some other non-visual inspection means.

In operation it can be seen that if, for example, control cable 68a is put under tension that a compressive force would be exerted upon the vertebrae assembly 36. Each vertebrae 52, being disposed along flexible member 60, is free to rotate about the pivot formed by the abutment of the vertebrae 52 pivot ridges 53 with the pivot ridges 53 of adjacently disposed vertebrae 52. Thus an overall flexure of the vertebrae assembly will occur, the direction of flexure being upwards in a vertical plane normal to the plane through the pivot ridges 53. As a greater amount of tension is placed upon cable 68a a greater degree of flexure will occur. Ultimately the upper tapered faces of adjacent vertebrae will butt together, at which time the flexure will cease. As can be readily appreciated, the total amount of flexure possible is a function of the aforementioned operating angle B shown in FIG. 5.

In a similar manner, flexure will occur in a downward direction within a vertical plane if the off-axis cable 68b is placed under tension instead of cable 68a. This is true even though cable 68b is offset from the vertical centerline of the objective head 38 and vertebrae assembly 36, such that a tension in cable 68b would normally cause a downward flexure along a plane passing through offset cable 68b and the center of the vertebrae assembly 36. As was discussed above, member 60 is of a substantially rectangular shape and has a substantially rectangular cross sectional area. Such a three-dimensional geometry, in conjunction with the aforementioned stiffness of member 60, resists a force which would cause a torsion about the longitudinal centerline of member 60. Thus the torque exerted by the tension within off-axis cable 68b is resisted, the resulting direction of flexure being substantially downward in FIG. 3D, such as substantially within the vertical plane normal to the horizontal plane of member 60.

The resistance to torsion of member 60 is an important feature of this embodiment of the invention, as has been previously discussed, for torqueing forces may also be encountered by the objective head 38 or vertebrae assembly 36 as they pass through the inner cavities of a structure under examination. A resistance to torqueing forces results in an inspection instrument constructed in a relatively simple, low cost manner having a torque resistance which prevents unintended excessive torsional movements of the objective head as it passes through the interior regions of a cavity such as the human colon.

Referring now to FIG. 7 and FIG. 8, an alternate embodiment of the invention is shown wherein the flexible member is comprised of two members 96 disposed within diametrically opposing channels 94 made in the outer cylindrical wall of each of the vertebrae 90. Each member 96 has a substantially rectangular cross-sectional area in accordance with the invention, whereby each member imparts torque stability to the vertebrae. Each of the channels 94 are symetrically disposed about a horizontal plane passing through pivot ridges 108, whereby the vertebrae 90 may pivot relative to one another and the opposing face of an objective head 102 and a transitional coupler (not shown). An end 106 of each flexible member 96 is formed as, for example, a partial spiral shape such that it may be fixed by a pin 110 or soldered within an appropriately shaped groove 104 made in the objective head 102. A rearward end of each member 94 (not shown) is similarly shaped and fixed within a similar slot made within the transitional coupler (not shown).

A central aperture 92 of each vertebrae 90 has a pair of diametrically opposed hanger-like structures 98 formed upon the aperture wall. Structures 98 are disposed symetrically about a vertical plane which is normal to the horizontal plane passing through pivot ridges 108. A control cable 100 passes through each structure 98, the forward end of which is anchored within objective head 102. Tension placed on a control cable 100 by the control assembly (not shown) will cause a flexure in member 96, resulting in vertebrae 90 and objective head 102 moving in an arc within the vertical plane normal to the horizontal plane passing through pivot ridges 108.

Referring to FIG. 9, another embodiment of the invention is shown wherein the pair of members 96, each of which having a substantially rectangular cross section to achieve torque stability, is enclosed within a pair of interiorly disposed channels 112 formed within the wall of an aperture 92 made within vertebrae 90. The advantage to be gained by disposing the pair of members 96 within the aperture 92 is that the resulting articulating vertebrae assembly is safer for use in endoscopic inspection instruments. This is for the reason that if a mechanical failure of a flexible member occurs, the member cannot readily escape from the instrument, possibly harming the patient being examined.

FIG. 10 is similar to the embodiment of the invention as shown in FIG. 9, the difference being that the interiorly disposed channels 114 are left open, and hence are of a simpler construction than the channels shown in FIG. 9.

FIG. 11 shows yet another embodiment of the invention wherein a single member 96, of substantially rectangular cross-sectional area, is centrally disposed within aperture 92, the member being contained within a conduit channel 118 formed in a centrally disposed conduit 116. The conduit 116 supported by a plurality of spoke-like supports 120 integrally joining conduit 116 to vertebrae 90.

FIG. 12 shows still one further embodiment of the invention, wherein the flexible member 122 is of square or circular cross sectional area and is contained within a centrally disposed conduit 116 supported within aperture 92 by spoke-like supports 120. The embodiment of FIG. 12 further contains a second pair of diametrically opposed control cables 100, such that four control cables 100, each 90 degrees from the two adjacent, are disposed about the wall of aperture 92 within hanger-like supports 98. Such an arrangement of control cables permits a four-way articulation of the objective head (not shown in FIG. 12), the articulation being in both a vertical and a horizontal plane. Of course, if such a four way deflection is desired, it is necessary that the individual vertebrae 90 be of a shape that permits such a deflection. The aforementioned U.S. Pat. No. 4,530,568 describes one possible shape for such a vertebrae 90.

It is to be understood that the above described embodiments of the invention are illustrative only, and that modifications thereof may occur to those skilled in the art. Accordingly, the invention is not to be regarded as limited to the embodiments disclosed herein, but is to be limited only as defined by the appended claims.

What is claimed is:

1. A torsion resistant vertebrae assembly having a base end member at one end thereof and an articulating end member on an opposite end thereof, said articulating end member having means to control the position thereof relative to said base end member, said vertebrae assembly comprising:
   a plurality of individual vertebrae adjacent one another, each of said vertebrae adapted to articulate to its adjacent one;
   control means for repositioning said articulating end member relative to said base end member, said control means being attached to said articulating end member and being activated on said base end member end of said assembly;
   holding means for holding said base end member together with said articulating end member and said plurality of individual vertebrae disposed therebetween, said individual vertebrae operable to articulate one on another as controlled by said control means; and
   resilient stiffening means disposed along said individual vertebrae in a manner in which said vertebrae are moveably coupled with said stiffening means whereby as said articulating end member of said assembly is articulated by said control means, said stiffening means provides torsion resistant controlled repositioning of said articulating end member.

2. A torsion resistant vertebrae assembly as defined in claim 1 wherein said holding means is said stiffening means.

3. A torsion resistant vertebrae assembly as defined in claim 1 wherein said articulating end member is an objective head of a flexible inspection device.

4. A torsion resistant vertebrae assembly as defined in claim 1 wherein said base end member is a collar means attached to an end of a flexible inspection means.

5. A torsion resistant vertebrae assembly as defined in claim 1 wherein said resilient stiffening means is a leaf-type spring means.

6. A torsion resistant vertebrae assembly as defined in claim 5 wherein said vertebrae have a center opening such that said stiffening means may pass therethrough.

7. A torsion resistant vertebrae assembly as defined in claim 5 wherein said spring means comprises at least two separate spring members each of which is disposed at different positions on said vertebrae.

8. A torsion resistant vertebrae assembly as defined in claim 1 wherein said vertebrae have a center hollow portion therethrough, and wherein said stiffening means is a wire member disposed through said hollow portion, said vertebrae further comprised of spoke-like members extending towards said wire member and holding said wiremember in position relative to said vertebrae.

9. A torsion resistant verterae assembly as defined in claim 1 wherein said vertebrae are of an annular shape.

10. In an inspection instrument having a generally cylindrical, elongated flexible body extending between a control assembly at a proximal end thereof and a distal head at a distal end thereof for viewing subject matter to be inspected, and further comprising:
    an articulated vertebrae assembly comprised of a plurality of individual vertebrae, said assembly having a first and a second end, said first end of which is disposed adjacent said distal head, said assembly capable of deflection in at least two discrete directions;
    a transitional coupler disposed at said second end of said vertebrae assembly for coupling said assembly to said flexible body;
    a resilient stiffening means disposed along said vertebrae assembly in a manner in which said vertebrae are moveably coupled with said stiffening means; and
    control means for controlling the position of said objective head disposed through said body, said control means being anchored to said distal head and being activated at said control assembly.

11. An instrument as set forth in claim 10 wherein said stiffening means comprises:
    a substantially rectangular member of a given length, width, and thickness, said member having a substantially rectangular cross-sectional area.

12. An instrument as set forth in claim 11 wherein said member further comprises:
    a plurality of substantially rectangular members having the same said given length and width, each of said members further having a substantially rectangular cross-sectional area and a thickness such that said members may be stackably disposed in a leaf-like spring arrangement wherein the overall thickness of said arrangement equals the and given thickness.

13. An instrument as set forth in claim 12 wherein said member is fastened at a first end to said distal head and at a second end to said coupler, whereby said individual vertebrae are flexibly urged together.

14. An instrument as set forth in claim 13 wherein said member further comprises:
    a first pair of slots oppositely disposed near said first end of said member and a second pair of slots oppositely disposed near said second end of said member.

15. An instrument as set forth in claim 14 wherein:
    each of said distal head, said coupler, and said vertebrae assembly have an opening disposed longitudinally therethrough, each of said openings further having a pair of channels disposed within for containing an edge of said member therein.

16. An instrument as set forth in claim 15 further comprising:
a first and second pair of openings disposed through said distal head and said coupler, respectively, whereby said member may be fastened at said first and second ends by pins inserted through said first and second pair of openings, said pins engaging said slots whereby said distal head and said vertebrae assembly are fastened to said coupler.

17. An instrument as set forth in claim 16 wherein said vertebrae assembly further comprises:
said plurality of individual vertebrae, each of said vertebrae of annular shape and adjacently disposed, each of said vertebrae having two opposing faces tapered to form oppositely extending pivot ridges, said ridges coplanar with said member, said ridges of said adjacent vertebrae flexibly urged against one another by said distal head, said coupler, and said pinned member.

18. An instrument as set forth in claim 17 wherein:
said control cables are substantially diametrically disposed in a plane normal to said member whereby when said tensioning means tensions one of said cables, said member will bend in a direction along said plane normal to said member thereby causing said plurality of vertebrae to pivot about said pivot ridges.

19. An inspection instrument as set forth in claim 10 wherein said articulated vertebrae assembly further comprises:
a plurality of adjacently disposed vertebrae each of which having a centrally disposed first opening made longitudinal therethrough, each of said vertebrae further having two opposing faces tapered to form oppositely extending pivot ridges, said opening containing a centrally disposed conduit extending longitudinally therethrough, said conduit having a second opening made longitudinally therethrough, said conduit connected to a wall of said first opening by a plurality of spokelike supports attached at a first end to said wall and at a second end to an outer surface of said conduit.

20. An inspection instrument as set forth in claim 19 wherein a linear portion of said member is contained within said conduit, said member being disposed within a plane passing through said pivot ridges.

21. An inspection instrument as set forth in claim 10 wherein said stiffening means is of a shape that resists torsion about its longitudinal axis.

22. In an inspection instrument having a generally cylindrical, elongated flexible body extending between a control assembly at a proximal end thereof and a distal head at a distal end thereof for viewing subject matter to be inspected, and further comprising:
an articulated vertebrae assembly comprised of a plurality of individual vertebrae, said assembly having a first and a second end, said first end of which is disposed adjacent said distal head, said assembly capable of deflection in at least two discrete directions;
a transitional coupler disposed at said second end of said vertebrae assembly for coupling said assembly to said flexible body;
a resilient stiffening means disposed along said vertebrae assembly in a manner in which said vertebrae are moveably coupled with said stiffening means, wherein said stiffening means comprises:
two substantially rectangular members of a given length, width, and thickness, each of said members having a substantially rectangular cross-sectional area; and wherein said instrument further comprises:
control means for controlling the position of said objective head disposed through said body, said control means being anchored to said distal head and being activated at said control assembly.

23. An inspection instrument as set forth in claim 22 wherein each of said members further comprises:
a plurality of substantially rectangular members having the same said given length and width, each of said members having a substantially rectangular cross-sectional area and a thickness such that when said members are stackably disposed in a leaf-like spring arrangement that an overall thickness of said arrangement equals the said given thickness.

24. An inspection instrument as set forth in claim 23 wherein:
said distal head, said coupler, and said vertebrae assembly each have a pair of diametrically opposed slots made longitudinally within an outer surface, each of said slots of a given width and depth suitable for containing one of said members therein, said slots in said distal head and said coupler further being suited for anchoring an end of said member contained therein.

25. An inspection instrument as set forth in claim 22 wherein said vertebrae assembly further comprises:
a plurality of adjacently disposed vertebrae each of which having an opening therethrough, and further having two opposing faces tapered to form oppositely extending pivot ridges, said opening having an interior wall, said wall having attached thereto a pair of diametrically disposed hollow conduits, each of said conduits having at least three interior walls, each of said conduits suitable for enclosing a linear portion of one of said members passing therethrough, said members being disposed within a plane passing through said pivot ridges.

26. In an inspection instrument having a generally cylindrical, elongated flexible body extending between a control assembly at a proximal end thereof and a distal head at a distal end thereof for viewing subject matter to be inspected, and further comprising:
an articulated vertebrae assembly comprised of a plurality of individual vertebrae, said assembly having a first and a second end, said first end of which is disposed adjacent said distal head, said assembly capable of deflection in at least two discrete directions;
a transitional coupler disposed at said second end of said vertebrae assembly for coupling said assembly to said flexible body;
a resilient stiffening means disposed along said vertebrae assembly in a manner in which said vertebrae are moveably coupled with said stiffening means, said stiffening means having a shape that resists torsion about a longitudinal axis thereof and wherein said shape is a rectangular cross-sectional shape; and
control means for controlling the position of said objective head disposed through said body, said control means being anchored to said distal head and being activated at said control assembly.

27. A torsion resistant vertebrae assembly having a base end member at one end thereof and an articulating end member on an opposite end thereof, said articulating end member having means to control the position thereof relative to said base end member, said vertebrae assembly comprising:

a plurality of individual vertebrae adjacent one another, each of said vertebrae adapted to articulate to its adjacent one;

control means for repositioning said articulating end member relative to said base end member, said control means being attached to said articulating end member and being activated on said base end member end of said assembly;

holding means for holding said base end member together with said articulating end member and said plurality of individual vertebrae disposed therebetween, said individual vertebrae being in contact with and operable to articulate relative to one another as controlled by said control means; and a resilient stiffening means disposed along said individual vertebrae in a manner in which said vertebrae are moveably coupled with said stiffening means whereby as said articulating end member of said assembly is articulated by said control means, said stiffening means provides torsion resistant controlled repositioning of said articulating end member.

* * * * *